United States Patent [19]

Klein

[11] 4,129,647

[45] Dec. 12, 1978

[54] TREATMENT OF ACNE

[76] Inventor: Edmund Klein, 1325 N. Forest Rd., Williamsville, N.Y. 14221

[21] Appl. No.: 843,053

[22] Filed: Oct. 17, 1977

[51] Int. Cl.$^2$ .................... A61K 39/02; A61K 31/505
[52] U.S. Cl. ........................................ 424/92; 424/251; 424/349
[58] Field of Search .................... 424/78, 251, 349, 92

[56] References Cited

U.S. PATENT DOCUMENTS

| | | | |
|---|---|---|---|
| 3,423,508 | 1/1969 | Krishnamurthy et al. | 424/251 |
| 3,472,931 | 10/1969 | Stoughton | 424/251 |
| 3,535,422 | 10/1970 | Cox et al. | 424/164 |
| 3,551,554 | 12/1970 | Herschler | 424/251 |
| 3,671,643 | 6/1972 | Kalopissis | 424/330 |
| 3,886,278 | 5/1975 | Gallo | 424/267 |
| 3,891,757 | 6/1975 | Higuchi | 424/251 |
| 3,954,758 | 5/1976 | Schumon et al. | 424/251 |
| 3,989,815 | 11/1976 | Rajadhyaksha | 424/251 |
| 3,989,816 | 11/1976 | Rajadhyaksha | 424/251 |
| 4,017,626 | 4/1977 | Gauri | 424/251 |

OTHER PUBLICATIONS

Chem. Abst. 79, 76881(q), (1973)—Malaviya et al.
Chem. Abst. 75, 33053(w), (1971)—Nishioka et al.
Chem. Abst. 78, 144095(x), (1973)—Vakilzadeh et al.

Primary Examiner—Albert T. Meyers
Assistant Examiner—D. W. Robinson
Attorney, Agent, or Firm—Cushman, Darby & Cushman

[57] ABSTRACT

A method for the immuno-therapeutic control and treatment of acne by administering an effective amount for treatment of an immunological preparation comprising an immunogen and at least one anti-mitotic adjuvant agent together with a pharmaceutically acceptable carrier.

9 Claims, No Drawings

TREATMENT OF ACNE

BACKGROUND OF THE INVENTION

This invention relates to the treatment of Acne Vulgaris (hereinafter sometimes referred to as "acne").

Acne is recognized as an inflammatory disease, very common at puberty, occurring in skin areas where sebaceous glands are largest and most active. There are a number of pathological processes which lead to the manifestation of acne. Changes occur in the quality and/or quantity of the sebum, an oily secretion produced by the sebaceous glands. These changes are associated with alterations in the secretory cells, in the sebaceous glands, and in the surrounding connective tissue elements. In areas of actual or potential hair growth, abnormalities of the hair follicles and hair may be associated with the disturbances in the sebaceous glands which are located in the immediate vicinity of the hair shaft. These glands open through their ducts into the hair root canal, thus forming a common anatomical structure, the pilosebaceous apparatus (PSA). The causes of disturbances in the structure and/or function of the sebaceous glands and/or the PSA leading to or predisposing to acne, are not known. The sex hormones and possibly other hormones may play a role in regulating the sebaceous glands and/or the PSA. Excessive lipids placed on the skin from exogenous sources are an example of a cause which can lead to a condition resembling acne.

The pathological mechanism underlying acne includes a number of steps. Inspissation of sebum at the external orifice of the sebaceous gland duct and/or the hair follicle leads to formation of a "plug" (comedone) which obstructs the flow of sebum. On exposure to oxygen, the comedone turns dark forming what is commonly referred to as a "black head". The water content of the comedone is reduced by evaporation and diffusion into the adjacent horny layer (keratin) of the surface epidermis resulting in a hardening of the comedone, starting at the external surface. The comedone may become attached to the keratin and thus "moored" to adjacent elements of the skin. The comedone becomes modified chemically, as well as physically, thus becoming a material which is foreign to the body. This state of "foreignness" should provoke an inflammatory reaction, including immune reactions and other responses of various defense systems, particularly those associated with granulocytes and macrophages. If the inflammatory reaction and the immune and other defense responses are effective in eliminating or containing the effects of the comedone, further progression of acne manifestations do not occur. Frequently, however, the immune and other defense reactions are not effective in terminating the acne process at this stage and the process progresses partly or wholly as described below.

While the comedone is obstructing the outlet of the duct, the sebaceous glands can continue to form sebum, which accumulates in the duct and in the glands, distending both. The distension and the resulting pressure lead to further intensification of the inflammatory reaction in the adjacent skin and subcutaneous tissues and produce additional swelling (edema), redness (erythema), discomfort, and a mass, which includes the obstructed and thefore encysted sebaceous gland ("redhead", "pimple", or acne papule). Frequently, the defense mechanisms are not adequate to terminate this process promptly at the acne papule stage and it continues to progress as outlined below.

The above conditions favor the growth of bacteria, and the resultant infections involve the duct, the sebaceous glands and the surrounding tissues, usually in that order. The onset of the infection produces further inflammatory changes, thereby initiating a vicious cycle causing continued and/or increased obstruction of the outflow of the sebum, which in turn leads to more pressure, more inflammation and continued or progressive infection. This leads to the formation of the acne pustule. The immune and other defense mechanisms having been inadequate to prevent these conditions from arising, frequently fail to arrest or reverse the process early in the acne pustule stage and it persists or progresses further.

Obstruction with or without infection leads to the formation of cysts. Infection of a cyst results in the formation of an abscess which leads to local tissue destruction. If this destruction of tissue has involved the connective tissue elements of the skin or subcutaneous tissues to a sufficient degree, healing is frequently accompanied and/or followed by scar formation.

The scars in acne can vary from minimal to extensive and severely disfiguring problems which are permanent sequallae of acne. While the process by which acne arises and lasts for an indefinite time may and frequently does come to a halt as a result of treatment or spontaneously, the scars persist for life unless they are removed, usually by a surgical method.

While there are many treatment methods which have been used, it is generally agreed that there is no uniformly satisfactory method for curing or even controlling acne. The therapeutic methods which are available, address themselves primarily to the palliative management of the manifestations of acne, (resulting from the abnormalities of the sebum and the sebaceous glands) such as oiliness, comedones, infections and scars. Representative of but a few of the many methods and compositions proposed heretofor for the treatment of acne, reference is made to U.S. Pat. Nos. 3,535,422; 3,663,716; 3,671,643; 3,867,522 and 3,886,278.

Accordingly, it is the primary object of the present invention to provide a treatment for and therapeutic control of acne.

This and other objects of the present invention will become more apparent from the discussion which follows.

SUMMARY OF THE INVENTION

The present invention provides for the treatment of acne by administering to a patient an immunogen in an amount sufficient to induce a delayed hypersensitivity reaction and thereafter applying to the skin of the patient, in an effective amount for treatment, an immunological preparation comprising an immunogen and at least one anti-mitotic adjuvant agent together with a pharmaceutically acceptable carrier.

DETAILED DESCRIPTION OF THE INVENTION

Treatment according to the present invention includes administering an effective amount for treatment of an immunological preparation comprising:

I. An immunogen;
II. An anti-mitotic adjuvant agent; and
III. A pharmaceutically acceptable carrier.

I have found that some of the difficulties encountered in controlling acne are due to mal-functioning of the humoral and/or the cellular components of the immune system. Defects in cellular immunity may be present alone or in addition to abnormalities in humoral immunity. Immunity may be defective in general as well as in specific forms.

Defective immunity can be partially or completely corrected or compensated by the processes and agents illustrated below. These include immunogens which induce or augment general and specific immune activities and agents which intensify the effects of immunogens (i.e. adjuvant agents). Adjuvant agents are those which inhibit cellular multiplication with and without concurrent inflammatory reaction.

The essential aspects of the immuno-therapeutic methods outlined below relate primarily to the local administration and consequently local effects of the agents employed at the sites of the outbreak. However, since immunologic effects and other defense mechanisms can and usually do occur on the basis of generalized and systemic factors, beneficial therapeutic effects may occur at sites other than those under direct treatment. Furthermore, since one of the essential aspects of the immune system is its memory, immunologic effects and other defense systems stimulated by them, as well as the resultant therapeutic effects, may occur and continue to recur for many years after the treatment methods described herein, have been discontinued.

While immunogens, anti-mitotic agents and similar immunologic approaches have been proposed and found effective in the treatment of primary and secondary tumors of the skin and soft tissues, the pathological considerations and processes associated therewith fails to suggest the effectiveness of a similar approach to the control of acne (see for example — "Immunotherapeutic Approaches to the Management of Neoplasms", Natl. Cancer Inst. Monogr. 35, 1972; "Immunologic Approaches to the Management of Primary and Secondary Tumors Involving the Skin and Soft Tissues: A Review of a Ten-Year Program", by Klein et al, Transplantation Proceedings, Vol. VIII, No. 2 (June), 1975; "Progress in Immunotherapeutic Approaches to the Management of Neoplasms", by Klein, Perspectives in Cancer Research and Treatment, pages 51–58 (undated); "Tumors of the Skin", by Klein, New York State Journal of Medicine, Apr. 1, 1968; and "Modulation of Host Immune Resistance in the Prevention or Treatment of Induced Neoplasias", DHEW Publication No. (NIH) 77-893).

As used herein, the term immunogen refers to substances which on administration to a patient augment or induce a delayed hypersensitivity resulting in a challenge reaction. Preferred immunogens include dinitrochlorobenzene (DNCB) and Bacillus Calmette-Guerin Vaccine. However, other agents may also be used such as benzene sulfonic acids and fluoronated alkyls.

The term "adjuvant agent" as used herein refers to substances which inhibit cellular multiplication (i.e. mitosis). Concurrent inflammatory reaction may accompany administration of the adjuvant agent. The adjuvant agents which may be employed include 5-fluorouracil, uracil, methotrexate, 7-deazauridine, vinblastin, orotic acid, guanine, adenine, thymine, folic acid, derivatives of the foregoing agents and the biologically inactive optical and other isomers of metabolites such as L-glucose, levo-rotatory-amino acids and their derivatives. Antimetabolites, metabolites, their congeners and their derivatives with solubility in or affinity for lipids (including particularly those modified for that purpose) are particularly effective because of their solubility in and/or miscibility with DNCB (the immunogen) on the one hand and lipid components of sebum on the other hand. 5-fluorouracil has been found to be a particularly preferred and effective adjuvant agent.

The immunological preparations employed according to my invention may be used in the form of a cream, gel, milk, aqueous or alcoholic solution, dermatogical cake or aerosol foam but preferably as a gel. Thus, the immunogen and at least one adjuvant agent are combined with a pharmaceutically acceptable carrier to form an immunological preparation having the desired physical characteristics. Suitable pharmaceutically acceptable carriers are well known in the art, as described for example in the aforementioned U.S. Pat. Nos. 3,535,422; 3,663,716; 3,671,643; and 3,886,278, each of which is incorporated herein by reference.

The present invention deals directly with the cause of acne, namely the formation of excessive and/or abnormal sebum, as well as with the secondary infections which follow the disturbances in the function and/or structure of the sebaceous glands which are largely responsible for some of the immediate effects such as pustules and abscesses, as well as the long-range effects of scarring acne.

Induction or potentiation of immunity, as brought about by this invention, facilitates the control of infection. The administration of agents which inhibit cellular multiplication, used as adjuvants for potentiating immune responses, in addition reduces the amount of sebum formed by reducing the number of sebaceous gland cells which are able to divide and multiply to form the secretory cells which undergo dissolution in order to produce sebum.

The sebum is a secretion which is formed by lysis of the whole sebaceous gland cells. Contrary to other glands, in which the secretion is formed by extrusion of a part of the glandular cell which continues to be secreted as long as the cell remains alive and functioning, the sebaceous gland is a holocrine gland in which death and dissolution of the secretory cell is required to form the secretion. Since the secretion of sebum is a continuous process, the number of cells which undergo lysis to form the secretion is vary high. Therefore, the corresponding number of cells have to multiply and produce cells which mature in order to form sebum. The constant flow of sebum particularly abundant when oiliness is excessive as in acne, requires the sebaceous gland cells which occupy a comparatively small space, to be highly active and to multiply at a high rate in order to provide sufficient sebum to cover comparatively much larger areas of the body surface. The cells of the sebaceous glands therefore are probably the most rapidly multiplying normal cells in the human body.

As a general rule, the more rapidly cells are multiplying, the more vulnerable they are to the effects of agents which inhibit cellular multiplication. Therefore, when agents are administered, which inhibit cellular multiplication, they have a considerably more intense effect on rapidly multiplying cells than on those which multiply more slowly. Since the sebaceous gland cells are probably the most rapidly multiplying normal cells on and near the body surface, agents which inhibit mitosis, affect them much more intensely than other cells in or near the skin such as the epithelial cells of the surface epidermis and the connective tissue elements in the dermis and subcutaneous tissue. The administration to the skin surface of agents which inhibit cellular multiplication, therefore, results in marked reduction in the amount of sebum produced. This in turn markedly reduces the tendency towards oiliness, comedone formation, cyst formation, and in general the conditions which favor the development of acne and subsequent scar formation.

Infection which results in acne is of course dependent on the multiplication of microorganisms. Induction or potentiation of immunity both specific against the offending microorganisms, and in general by stimulating cellular and non-cellular components of the immune and other defense mechanisms, facilitates the elimination and control of the acne. Furthermore, local application to the skin surface of adjuvant agents (e.g., 5-fluorouracil and/or uracil) which inhibit cellular multiplication, prevents, inhibits and leads to the more rapid resolution of the acne process than would occur otherwise (a) by stimulating the action of locally applied immunogenic agents and (b) by their direct action on inhibiting the growth of microorganisms. Therefore, the topical administration to sensitized patients of adjuvant agents which inhibit cellular multiplication further facilitates the control of acne.

Some of the difficulties in controlling severe cystic acne are associated with mal-functioning of the humoral and/or the cellular components of the immune system. This is indicated by abnormalities in the subcategories of the beta and/or gamma globulins and the specific antibody titres in the serum and, particularly, in the infected sebum. More commonly, above or in addition to abnormalities in humoral immunity, defects in cellular immunity are present. Defects in humoral and/or cellular immunity may be general or specific. Thus, in patients with severe acne responses to primary antigens may be low or absent. Furthermore, the time required for primary or secondary immune responses may be considerably longer than in normal individuals, the concentration of sensitizing agent required for inducing primary or secondary immune responses may be considerably higher and the levels of responses may be considerably lower than in the normal population. Levels of responses are indicated by the intensity of primary or secondary responses (if they occur), as related to the doses of the immunogen and the degree to which the concentration of the primary antigen (or hapten) can be decreased upon challenge to give a (minimal) skin test reaction (i.e. the higher the immunologic responsiveness, the lower the concentration of the sensitizing agent required for inducing a primary or secondary reaction).

In addition to the abnormalities in the response to primary antigens, alterations in immunologic memory as indicated by lowered or absent responses to recall antigens are noted. Since recall antigens are usually of microbial origin (but could be of any kind), a lack of response to them is clearly of significance in regard to the patient's susceptibility to and the pathogenesis of the acne process which occurs.

There may be considerable variations in cell mediated or delayed hypersensitivity responses to some primary or recall antigens as compared to other immunogens. Possibly of greater significance is the fact that the intensity of the delayed hypersensitivity challenge responses to the same concentrations of the same immunogens can vary markedly at different anatomical sites in the same patient. Thus, in the presence of significant skin test responses on the forearm or on the back, markedly reduced or no responses occur on the face when it is the site of significant acne. This suggests that regional as well as general factors play a role in immunologic responses and their defects. Immune responses are often defective in areas in which acne is present.

Induction or potentiation of immune reactions in response to local administration of immunogens occurs when various types of adjuvant agents, which alone may not be immunogenic, are concurrently adminstered locally at the same sites. The increased intensity of the immune reactions brought about by the adjuvant agents with or without inflammatory action, improves the therapeutic effects of immunotherapy in acne as compared to the therapeutic efficiency of immunotherapy without the adjuvant agent. A number of the adjuvant agents have therapeutic effects by themselves in these conditions, (i.e., without concurrent immunotherapy). However, these effects of adjuvant agents are considerably less marked when they are used by themselves than when they are combined with immunotherapy.

The adjuvant agents which inhibit cellular multiplication, exert their antimitotic effects by at least one of several different mechanisms. One group of agents, the antimetabolites, inhibit cellular multiplication and/or other metabolic activities essential for cellular survival by displacing or competing with normal metabolites (and/or substitutes for them) by structural analogy.

An alternate mechanism for accomplishing similar ends, namely inhibition of metabolic activities (e.g. cellular multiplication, respirations, protein synthesis or other normal metabolic activities) is through "substrate inhibition." In this process one or more normal metabolites, their substitutes, or their congeners are administered in large excess as compared to the amounts of concentration at which they are present under physiological conditions in the cell or other respective biological systems. When present in large excess, "substrate poisoning" occurs by which functional groups on the respective enzymes and/or other essential components of the respective metabolic systems are so overloaded by the normal metabolites (which are being administered in excess) that they are unable to deal with the normal substrates or congeners in a usual or alternate effective manner and thereby the metabolic process concerned becomes inhibited or comes to a halt. One may consider that the conformational states of the agents at high concentrations differ from their conformational states at lower concentrations and in this manner may inhibit or compete by "conformational" analogy. The mechanism of substrate inhibition then also results in inhibition of normal metabolic activities, such as cellular multiplication or processes like respiration and synthetic pathways upon which cell survival or division is dependent.

A further mechanism which may lead to inhibition of cellular multiplication is by administration of excessive amounts of co-enzymes (e.g., thiamine) or other co-factors (essential or auxilliary, e.g., magnesium) which have inhibitory effects on essential enzymes or other components of metabolic systems.

Generally, the method for therapeutic control and treatment of acne according to the present invention is an immunotherapeutic approach involving the following procedures:

(a) Inducing delayed hypersensitivity to an immunological preparation which is applied by an occlusive patch-test technique (immunogen applied at concentrations of 0.001 to 20% and preferably 0.1 to 1.0% by weight of the preparation) until a hypersensitivity challenge reaction appears;

(b) Titrating by serial dilution the immunogen (level of adjuvant agent being held constant at between about 0.001 to 50% by weight of the preparation) to determine the lowest concentration (referred to herein as the "effective amount for treatment") of the immunogen to which the patient develops a minimal delayed hypersensitivity challenge reaction, and constitutes a "sensitized state". Generally, the minimal concentrations (i.e. effective amount for treatment) of immunogen for the induction of a challenge reaction or sensitized state ranges from 0.1 to 0.0000001%.

The challenge response at acne sites is generally more intense than in normal tissues and thus a concentration one or two orders of magnitude below the lowest concentration to which a delayed hypersensitivity challenge reaction could be demonstrated in normal skin is applied to areas of acne infestation.

In general the immunological preparations used according to the present invention comprise by weight 0.0000001 to 20%, and more often 0.001 to 1.0% of a immunogen; 0.001 to 50% and preferably 0.1 to 20% of at least one adjuvant agent, the balance of the preparations constituting a pharmaceutically acceptable carrier. The carrier constitutes at least 50% by weight of the preparation. It will be appreciated by those of ordinary skill in the art that the amounts of immunogen and adjuvant agents needed to induce a sensitized state and be effective for treatment will vary within these limits depending upon the specific agent employed and the reaction of the patient being treated. Generally, in order to induce a challenge reaction (i.e. induce hypersensitivity) from about 10 to 100 mg of the preparation is applied by a standard occlusive patch test technique. Upon determination of the effective amount for treatment, appropriate amounts are applied topically to the area where acne is present.

Administration of the immunological preparation need not be limited to the site of clinically detectable involvement, but may be extended over the anatomical region where the acne is located. The minimum effective amount of the immunogen may increase or decrease during the course of applications.

During this period, afflicted areas undergo one or more of the successive stages of delayed hypersensitivity reactions. Following maintenance of a sensitized state for variable periods, the acne subsides accompanied by repair and reepithelialization.

In principle, the processes carried out to induce or potentiate immune responses entail the following steps: A immunogen (e.g., a hapten like Dinitrochlorobenzene-DNCB, or a complete antigen like mumps antigen) is applied as a gel or in another suitable vehicle under a cover to the volar surface of the forearm in the same manner as a routine patch test (topical, percutaneous). Alternatively, primary (or secondary) sensitization can be carried out by other routes of administration depending on the nature of the immunogen and the vehicle (e.g., intracutaneous, subcutaneous, intramuscular, intravenous, or oral). The concentration of DNCB used as a primary antigen for the initial sensitizing procedure (i.e. augment or induce a delayed hypersensitivity) is generally one part of DNCB per thousand parts of vehicle (0.1%) when DNCB is the sensitizing hapten and the convenient topical route is used. Appropriate adjustments of the dose of immunogens have to be made when other immunogens are used depending on their nature, the vehicle and the route of administration.

The principles of the procedures, however, are essentially the same, regardless of the immunogen, adjuvant agent and the pharmaceutically acceptable carrier as well as the route of administration. These principles will be illustrated by the use of DNCB but it is to be noted that other immunogens may be equally effective.

The following Examples are offered to facilitate a fuller understanding of the invention but, are not to be construed as limiting the scope thereof.

EXAMPLE 1

Approximately 20–50 mg. of K-Y gel available from Johnson and Johnson containing 1:1000 of DNCB is used. This preparation is applied daily under occlusion for a period of 4 weeks or less if a reaction occurs. Daily applications of the sensitizing preparations are carried out at as close to the same anatomical sites as possible.

Concurrent topical administration of an adjuvant agent, 5-fluorouracil and/or uracil, greatly enhances the induction and/or manifestations of immune reactions due to locally applied immunogenic preparations, such as DNCB. Therefore, the respective concentrations of DNCB as a single agent and in combination with one or more adjuvant agents are applied to separate sites. Thus, preparations of DNCB (at appropriate concentrations) as well as mixtures of DNCB (at the same concentrations) and 5-fluorouracil (usually about 0.1% to 0.5%) and/or uracil (from about 0.1% to 20%) are each applied at one or more other sites as outlined below.

As soon as a reaction is noted, the patient on prior instruction discontinues the application of the respective immunological preparation and reports the onset of a reaction. A reaction may start by any awareness of a change, usually itching or slight burning at the site of application of the preparation. Alternatively, or in addition, slight swelling, redness or vesicle formation may occur. Any of these phenomena may become apparent during application of the immunogen or after discontinuation. The onset of a delayed hypersensitivity reaction constitutes the sensitized state.

Following primary induction of a hypersensitive response to DNCB with or without concurrent adjuvant agents, progressively lower concentrations (preferably 10 fold serial dilution) of the immunological preparation are applied by an occlusive patch test technique in order to determine the minimum concentrations of DNCB with and without adjuvants to which the patient shows a minimal skin test reaction.

Following determination of a concentration of DNCB which as a single agent or in the presence of one or more adjuvant agents as predetermined concentrations produces a minimal challenge or hypersensitivity reaction on the forearm, the same concentrations of both the immunogen and the adjuvant agents as single agents and in combination with one another are explored on the skin involved by acne, preferably at relatively inconspicuous anatomical sites, such as the angle of the jaw, if the face is involved. Depending on the degree of the response at the test site within the area involved by acne, the concentrations of the immunogen and/or the adjuvant agents are adjusted (i.e., increased and/or decreased, respectively) to induce an appropriately mild erythematous reaction. This is the effective amount for treatment and the immunological preparation is then applied topically without occlusion to the entire area once, twice or more often per day as indicated by the clinical response. A course of single or multiple daily applications may vary from several days to several months on a continuous or intermittent basis in order to induce adequate therapeutic results. During the course of administration of the agents the concentrations may be varied from one time to another and/or from one anatomical site to another, as indicated by the clinical response.

Results

The immunologic treatment in conjunction with adjuvant agents leads to inhibition of cellular multiplication of the sebaceous gland cells as well as to arresting the growth of bacteria in the control of acne, ranging from the mild to the severe cystic and conglobate types of the disease. Topical administration of solutions, ointments and creams, gels, sprays and other vehicles (preferably gels) containing immunogens and adjuvant agents have been carried out and found to result in marked reduction and/or elimination of the various aspects of acne, as described above.

EXAMPLE 2

In those patients in whom a challenge reaction to the immunological preparations described above does not occur in the initial four week period, a higher concentration of DNCB (one part of DNCB to 100 parts of vehicle is used) and/or the concentrations of adjuvant agents are increased to effective levels (e.g. 5-fluorouracil up to 20% and uracil up to 50%, respectively). The procedures described in Example 1 are again carried out for another 4 week period.

In those patients in whom a reaction to the above procedure still does not occur after a 4 week period, skin tests to a group of microbial antigen (e.g. Purified protein derivative of tuberculin (PPD), streptokinase-streptodornase (SK-SD), mumps antigen (MA), candida extract (CA), trichophyton (T), histoplasmin (H), and coccidioidin (Co) are carried out to determine whether immunologic memory has been retained, compromised, or lost. Alternatively, skin testing of recall antigen can be carried out as the initial step or concurrently with the primary sensitizing procedure as described for DNCB.

Following the skin test procedure for recall antigens, the patient is given a single dose of BCG vaccine by the oral route (40 mg BCG in water, orange juice, or other aqueous preparation). Alternatively, BCG may be administered intradermally or by the scarification method at appropriate doses. Also, other immunopotentiators (e.g., C. Parvum, Laevamisole) may be used. After a 2 week interval following the oral administration of BCG vaccine, the skin tests for recall antigens are repeated to determine the effect of BCG. If ineffective, BCG administration and the skin tests for recall antigens are repeated. If repeated BCG administration is not effective in potentiating immunity as indicated by lack of development or increased intensity of skin test responses, other methods of immunopotentiation such as administration of transfer factor are required.

If and when BCG administration is effective in potentiating immunity, the procedure described for inducing hypersensitivity to DNCB with or without concurrent adjuvants is started again. In the majority of patients a response to DNCB occurs following immunopotentiation as a result of administration of BCG.

If hypersensitivity to DNCB or another primary antigen, which can be well controlled in regard to the levels of challenge responses elicited but it cannot be induced, while responses to recall antigens (immunological memory) are present, the latter (e.g., PPD, SK-SD, etc.) can be employed topically (or by local injection) as described for and in lieu of, DNCB in Example 1.

Clinical Studies

Topical immunotherapy according to the present invention was studied in 32 patients with moderate to severe acne over periods ranging from 3 to 9 months. Partial to complete control was attained by these procedures in more than 90% of patients. Significant improvement was observed within 2 to 6 weeks of initiating treatment. Once adequate control of acne was induced, the intensity of the treatment could be reduced without significant recurrence in 50 to 60% of the patients. In 14% of the patients, all treatment for acne was stopped for observation periods of 3 to 6 months following courses of immunotherapy without significant recurrences. Patients were included in the initial study only if standard therapeutic modalities had been exhaustively explored and had failed. The patients selected for study had moderately severe to severe cystic acne with varying degrees of inflammation. The ages ranged from 16 to 43 years. The groups included 17 females and 15 males.

Standard hematology (CBC), clinical chemistry (SMA 12), plasma protein electrophoresis, quantitative immunoglobulins and immunoelectrophoresis determinations and urinalysis were carried out at the beginning of the study to exclude patients with abnormal findings and at intervals during the study. Skin test responses to dinitrochlorobenzene and recall antigens (PPD-purified protein derivative of tuberculin, Varidase-V, Trichophyton-T, Coccidiodin-Co, Candida extract-Ca, Histoplasmin-H) were determined prior to or during the study. If BCG administration was carried out, skin tests were repeated at appropriate intervals. As indicated, other tests were repeated at appropriate intervals.

Clinical Procedures

All patients were placed on standard therapy including specifically salicylic acid solutions ranging in concentration from 3% to 10% dissolved in 50% to 70% ethyl alcohol. If indicated, benzoxyl peroxide and retinoic acid preparations were added. In addition, patients were initially placed on tetracycline (250 mg. qid) which was subsequently replaced by erythromycin, as indicated by the clinical course; minocycline was added in doses ranging from 50 mg. to 200 mg. per day, depending on the degree of infection and the persistance of infected cysts. Patients who failed to respond after 6 months or longer on this regimen (supplemented by appropriate hygienic measures) were selected for study of the effects of topical immunotherapy.

Initially, patients were placed sequentially on one of the following four regimens: (a) immunogen with and (b) without adjuvant agents, (c) adjuvant agents without immunogen and (d) continued therapy by standard modalities without sensitizing or adjuvant agents (e.g. "controls").

In view of the marked therapeutic effects of the first three regimens of the study, as compared to the control (d) employing continued standard modalities alone, omission of the procedures used in (a), (b) and (c) was considered disadvantageous to the patient's best interests and the control arm was discontinued in the study group.

Results were assessed by counting lesions (comedones, cysts, papules, pustules) in symmetrical sites in the same patient after one side had received one form of therapy, while its counterpart had received no therapy or another form of therapy. Side effects were evaluated in terms of erythema, erosion, scaling and discomfort. After 2 to 6 weeks of concurrent bilateral comparison studies, sequential evaluation by the criteria outlined above was carried out. Evaluation of sequential results were based on serial photographs under standardized conditions throughout the study.

Patients were skin tested with immunogens described above. Test procedures included DNCB preparations with and without the concurrent administration of adjuvant agents. Adjuvant agents included uracil and 5-fluorouracil in an aqueous cream or gel, and were used for intensifying immune responses, particularly at lower concentrations of DNCB, as well as for their direct contributions to treatment. In addition, adjuvant agents were submitted to patch testing in the absence of immunogen.

Initial testing was carried out by a modified patch test technique. Aliquots of 50 mg of a preparation containing DNCB or DNCB and adjuvant agents as in Example 1, respectively, were applied topically under an occlusive dressing to areas approximately 1 cm. in diameter. Patch testing in this form was usually carried out on the volar surface of the forearm, although at times areas on the upper arms, the thighs, the back and the chest were employed. Comparative studies between effects in these areas did not reveal significant differences in skin test responses unless clinical abnormalities were present in the areas tested.

Initial concentrations of DNCB ranged from 1:100 to 1:1000. The concentrations of 5-fluorouracil ranged from 0.001% to 2.0% and the concentrations of uracil ranged from 0.01% to 40%.

Since initially the majority of patients were not immunologically sensitive to DNCB with or without adjuvant agents, applications of DNCB were continued to the same test area for periods of up to 4 weeks in order to induce hypersensitivity.

In order to induce hypersensitivity, application of DNCB at concentrations of 1:100 or 1:1000 was continued for periods of up to 4 weeks unless hypersensitivity became apparent earlier (average time 2-3 weeks). When hypersensitivity became manifest, the concentration of DNCB was decreased to determine the lowest level to which the patient showed a delayed hypersensitivity challenge response on the normal skin. If hypersensitivity to DNCB was not induced within a four week period, the concentration of DNCB was increased by one order of magnitude and patch testing at a higher concentration with and without adjuvants was carried out for an additional 4 week period.

If hypersensitivity to DNCB was not established at that time, an oral dose of 40 mg. of BCG was administered unless the patient on testing for recall antigen responses had shown a strong PPD reaction (i.e. induration greater than 4 cm in diameter and/or vesiculation greater than 1 cm in diameter). Following BCG administration, patch test applications of DNCB were resumed. Skin testing for recall antigen responses were repeated 2-3 weeks following BCG administration. Unless hypersensitivity to DNCB was induced within 4 weeks of BCG administration or the PPD response had developed to or beyond the levels stated above, oral BCG was again administered at a dose of 40 mg. The procedures were repeated as described above following the first administration of BCG.

Since the majority of patients became sensitive to DNCB after the second administration of oral BCG, further attempts at inducing hypersensitivity reactions were unnecessary except in three patients in whom BCG administration and follow-up procedures as described above were repeated. Two of these patients who failed to develop hypersensitivity to DNCB were scheduled for transfer factor administration from DNCB positive donors. Previous experience had shown that hypersensitivity to DNCB was established following transfer of immunity.

Determination of Minimal Effective Concentration of Sensitizing Agent

Following induction of hypersensitivity to DNCB, administration of serially diluted concentrations of DNCB with and without adjuvant agents was carried out. Serial dilution was usually carried out at sequential 10 fold dilutions. Preparations of three consecutive concentrations were applied by patch testing at a time with and without concurrent administration of adjuvant agents. Patch tests were left in place for periods of up to 14 days before they were considered to be negative. The lowest concentrations (minimum effective concentration — MEC) of DNCB with and without adjuvant agents to which the patients showed an immune challenge response, were determined.

Following determination of the MEC with and without adjuvant agents, the immunological preparation was applied at test areas in the regions involved by acne. On the face relatively inconspicuous sites, such as the angles of the jaws, were selected. On the back and chest areas which would produce minimal discomfort, such as the upper shoulder or pectoral areas were usually chosen. Depending on the degree of reaction, the concentrations of DNCB and adjuvant agents were adjusted upward or downward respectively in order to induce reaction causing minimal erythema and minimal or no discomfort (pruritis or burning). In the majority of patients (60%), however, the MEC was initially the same on the normal skin and at sites involved by acne. However, during treatment, it frequently became necessary to modify the concentrations of DNCB and/or of adjuvants in order to retain a therapeutically effective and yet acceptable level of reaction.

Following determination of the initial MEC at sites involved by acne, the application of DNCB and adjuvants was extended from the test sites to part, or the entire area, involved by acne. If the area involved by acne was extensive or if the status of the acne was of marked severity, extension from the test site to the entire area was carried out gradually. This was done because sites involved by severe infection reacted considerably more intensely than normal skin or those involved by mild to moderate degrees of acne. Even when extension of the areas to which DNCB and adjuvants were applied was carried out gradually, the severity of the reaction at times was such that the concentrations of either DNCB and/or the adjuvants had to be decreased to bring the response within the range of acceptibility. This did not alter the favorable results of the treatment.

Daily administration of DNCB and adjuvants was carried out by concurrent topical applications of both agents to the affected sites for at least 12 weeks and was continued as long as improvement was apparent. Frequency of administration was usually twice per day, although at times one or both agents were administered a third time. Conversely, if the reaction exceeded acceptable levels, then the number of administrations of one or both agents per day was reduced. At times administration of one or both agents was carried out at two or even three day intervals.

Hypersensitivity to DNCB was induced in 31 of the 32 patients studied. Of the 31 patients, 25 developed hypersensitivity to DNCB within 2 months without BCG administration. Topical administration of preparation of DNCB (0.1%) resulted in hypersensitivity in 19 patients within 4 weeks. Six patients, who did not develop hypersensitivity over a 4 week period by exposure to DNCB at concentrations of 0.1% became sensitized during a subsequent 4 week period when the concentration of DNCB was raised to 1%.

The other six patients who had not developed hypersensitivity after 8 weeks of exposure to DNCB received 40 mg. of BCG by mouth and developed the same degree of reaction whether adjuvants were present or not. Of the six patients two developed hypersensitivity to DNCB within 4 weeks of receiving the first dose of BCG, two patients after a second dose of BCG and two patients after the third dose of BCG.

Of the 32 patients in this group, one patient failed to become sensitized to DNCB after 7 doses of BCG, given at monthly intervals. The patient who did not develop hypersensitivity to DNCB, failed to respond to treatment with DNCB at concentrations of 0.1 and 1% with concurrent administration of up to 2.0% 5-fluorouracil and 40% uracil.

In 25 of 31 patients who became sensitized to DNCB, the MEC in the normal skin was at least 0.001% or less. In the remaining six patients, the MEC in normal skin was 0.01% in three patients, and 0.1% in the other three patients.

Testing in acne sites showed the same MEC as in the normal skin in 20 patients. In three patients it was lower (e.g. 1,000.000, 1:10,000.000 and 1:1,000,000.000, respectively). In five patients the initial MEC at the acne sites was higher than in the normal skin (e.g. 1:1000 in three patients, 1:100 in two patients).

In 9 of 17 female patients who exacerbated in relation to the menstrual cycle the MEC increased by 1-2 orders of magnitude as the severity of the acne increased periodically.

Of the 31 patients who became sensitized to DNCB at concentrations of 1% or 0.1%, 25 patients showed stronger reactions when 5-fluorouracil or uracil was administered at the same time, two showed about the same degree of reaction whether adjuvants were present or not, and three showed lower levels of reactions to the immunogen.

In 28 of the 31 patients who became sensitized to DNCB, virtually complete control of the active manifestations of acne occurred. In two of the other three patients, marked improvement, but not complete control, occurred. There were no therapeutic effects in one patient who became sensitized to DNCB as well as in one patient who failed to develop hypersensitivity to DNCB.

The earliest indications of improvement (e.g. 25% or more reduction in number of new and persisting lesions) occurred with 2 weeks in 12 patients. In an aggregate of 21 of the 28 patients, improvement was observed within 4 weeks and in 25 patients within 6 weeks. The remaining three patients improved more gradually so that progress could not be objectively established in less than 8 to 12 weeks. Improvement of 50% or more required approximately 4 weeks in nine patients, 6 weeks in 14 patients, 8 weeks in 17 patients. 10 weeks in 20 patients, 12 weeks in 24 patients and 16 weeks in the remaining 4 patients.

Improvement to the level of "adequate" control (e.g. two new lesions or less per week on the face, the neck, the back, the chest or the arms, or a maximum of six new lesions when three or more of these anatomical sites were involved), was attained within approximately 4 weeks in three patients, 6 weeks in seven patients, 8 weeks in 14 patients, 10 weeks in 17 patients, 12 weeks in 21 patients, 16 weeks in 25 patients and within 20-24 weeks in the remaining three patients.

The use of immunogens combined with adjuvants gave superior results to sensitizing agents alone and the adjuvants alone which in turn gave superior clinical results than standard therapeutic modalities alone. Immunotherapy showed improvement (25% or more reduction in new lesions and in the number of persisting lesions) earlier than the individual immunotherapeutic or chemotherapeutic agents alone. The number of patients in whom improvement occurred was larger, and the degree of improvement was greater at corresponding times within the treatment course than with sensitizing agents or adjuvant agents alone. The duration required for complete control was shorter and the number of patients in whom complete control was attained was larger with the immunological preparation than with immunogenous or adjuvant agents alone.

In the group of patients with acne described above, it was found that combined immunogen with adjuvant agents (immunological preparation for acne) results in control in more than 90%.

The invention in its broader aspects is not limited to the specific details shown and described, but departures may be made from such details within the scope of the accompanying claims without departing from the principles of the invention.

The invention may furthermore comprise, consist or consist essentially of the hereinbefore recited materials and procedures.

I claim:

1. A method for the therapeutic control and treatment of acne which comprises administering to a patient an immunogen selected from the group consisting of dinitrochlorobenzene and Bacillus Calmette-Guerin Vaccine which induces or potentiates an immune response on local administration in an amount sufficient to induce a delayed hypersensitivity reaction and thereafter applying to the skin of said patient an immunological preparation in an immunologically effective amount for the treatment of acne, said preparation comprising an immunogen selected from the group consisting of dinitrochlorobenzene and Bacillus Calmette-Guerin Vaccine together with a pharmaceutically acceptable carrier.

2. A method according to claim 1 wherein said immunogen is dinitrochlorobenzene.

3. A method according to claim 2 wherein the pharmaceutically acceptable carrier is a gel.

4. A method according to claim 1 wherein said immunogen is administered concurrently with at least one anti-mitotic agent.

5. A method according to claim 4 wherein the immunogen is dinitrochlorobenzene and the anti-mitotic agent is 5-fluorouracil.

6. A method according to claim 4 wherein said anti-mitotic agent is 5-fluorouracil, uracil or mixtures thereof.

7. A method according to claim 1 wherein said immunological preparation further comprises at least one anti-mitotic agent.

8. A method according to claim 7 wherein said anti-mitotic agent is 5-fluorouracil, uracil or mixtures thereof.

9. A method according to claim 1 wherein said immunogen is administered concurrently with at least one anti-mitotic agent to induce said hypersensitivity reaction and said immunological preparation further comprises at least one anti-mitotic agent.

* * * * *